United States Patent [19]
Goldman

[11] Patent Number: 6,056,971
[45] Date of Patent: May 2, 2000

[54] METHOD FOR ENHANCING DISSOLUTION PROPERTIES OF RELATIVELY INSOLUBLE DIETARY SUPPLEMENTS AND PRODUCT INCORPORATING SAME

[75] Inventor: Robert Goldman, Cresskill, N.J.

[73] Assignee: Biosytes USA, Inc., Tenafly, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/899,454

[22] Filed: Jul. 23, 1997

Related U.S. Application Data

[60] Provisional application No. 60/022,564, Jul. 24, 1996.

[51] Int. Cl.$^7$ ........................................... A61K 9/48
[52] U.S. Cl. ............................. 424/439; 424/456
[58] Field of Search ...................... 424/456, 439

[56] References Cited

U.S. PATENT DOCUMENTS

| | | | |
|---|---|---|---|
| 4,572,915 | 2/1986 | Crooks | 424/284 |
| 5,532,002 | 7/1996 | Story | 424/456 |

OTHER PUBLICATIONS

Chem. abstr., vol. 123, 1995 (Columbus, OH, USA), the abstract No. 92898, Ribier, A. "Cosmetic Composition Made of an Oil in Water Emulsion Based on Oily Globules Coated with a Lamellar Liquid Crystal Coating." EP 641557 A1 1955.

Chem. abstr., vol. 118, 1992 (Columbus, OH, USA), the abstract No. 66767, Cole, S.K. "Studies Using a Nonionic Surfactant Containing Drug Delivery System Designed for Hard Gelatin Capsule Compatibility." Int. J. Pharm. 1992, 88 (1–3), 211–220.

Chem. abstr., vol. 115, 1991 (Columbus, OH, USA), the abstract No. 160932, Tomka, I. "Enca½sulation of Materials by Starch." DE 4002257 A1 1991.

*Primary Examiner*—Thurman K. Page
*Attorney, Agent, or Firm*—Aufrichtig Stein & Aufrichtig, P.C.; Peter D. Aufrichtig

[57] ABSTRACT

A method for enhancing the dissolution properties of relatively insoluble dietary supplements is provided in accordance with the invention. The method includes the steps of providing at least one relatively water insoluble dietary supplement, solubilizing the dietary supplement with a solubilizer, and incorporating an edible polyhydric alcohol into the solubilized dietary supplement to provide a liquid dietary supplement composition that will dissolve spontaneously in the gastrointestinal tract with the minimum agitation which normally occurs there due to peristaltic action. The liquid dietary supplement composition can be readily supplied by incorporation in a gelatin capsule and a gelatin capsule having a liquid dietary supplement incorporated therein is also provided in accordance with the invention. The gelatin capsule dissolves readily in the digestive tract and the dietary supplement has enhanced bioavailability in comparison to prior art gelatin capsules.

36 Claims, 3 Drawing Sheets

METHOD FOR ENHANCING DISSOLUTION PROPERTIES OF RELATIVELY INSOLUBLE DIETARY SUPPLEMENTS AND PRODUCT INCORPORATING SAME

This application is related to provisional 60/022,564 filed Jul. 24, 1996.

FIELD OF THE INVENTION

This invention relates generally to relatively water insoluble dietary supplements and, in particular, to a method for enhancing the dissolution properties of such relatively water insoluble dietary supplements and to a dietary supplement product having enhanced dissolution properties so that solution will take place spontaneously with the minimum agitation which normally occurs due to peristaltic action in the gastrointestinal tract.

BACKGROUND OF THE INVENTION

The use of dietary supplements is well known. For example, coenzyme Q-10 is a vitamin-like substance used around the world to treat congestive heart failure and other cardiac problems. In many countries, St. John's wort is widely recognized as useful for relieving depression as effectively as many antidepressant pharmaceuticals, but without unpleasant side effects. The list of such supplements is virtually endless.

One of the difficulties encountered in formulated such supplements for human ingestion is that many of the supplements are relatively water insoluble. Since the human digestive tract is a substantially aqueous system, it is difficult to provide these supplements in forms that will dissolve readily in the digestive tract and be available for use, i.e. bioavailable.

U.S. Pat. No. 4,572,915 issued to Crooks on Feb. 25, 1986 discloses aqueous formulations for fat soluble vitamins, essential nutrients, herb oils, and pharmaceutical agents. The formulations are prepared by first admixing the fat soluble vitamin, essential nutrient, or agent with a suitable amount of polyethoxylated castor oil and a pharmaceutically acceptable polyol, such as glycerol, to provide a non-aqueous phase. Thereafter, an aqueous phase containing mostly water and optionally a preservative, such as sodium benzoate, is slowly added to the agitated non-aqueous phase at an elevated temperature. The admixture is cooled and provided as a clear, homogeneous, micellized aqueous formulation.

It is often desirable to provide relatively water insoluble dietary supplements in a gelatin capsule form. Gelatin capsules, which can be hard or soft, are considered to be tasteless and easy to swallow. Furthermore, they dissolve readily in the digestive tract. Such capsules are filled with compositions that are provided to the digestive tract upon dissolution of the capsule.

One difficulty of using gelatin capsules arises because such capsules can not contain aqueous liquid compositions of the type disclosed in the Crooks patent. However, when non-aqueous compositions of relatively water insoluble dietary supplements are provided, the dietary supplement may not become bioavailable upon dissolution of the gelatin capsule.

It would, therefor, be desirable to provide a gelatin capsule containing a liquid composition of a relatively water insoluble dietary supplement that provides for enhanced bioavailability of the dietary supplement.

A goal of the invention is to provide a method for enhancing the dissolution properties of relatively water insoluble dietary supplements.

Another goal of the invention is to provide a dietary supplement product having improved dissolution properties.

A further goal of the invention is to provide a dietary supplement in the form of a gelatin capsule wherein the liquid dietary supplement contained therein has increased bioavailability.

Still other objects and advantages of the invention will in part be obvious and will in part be apparent from the specification.

SUMMARY OF THE INVENTION

Generally speaking, a method for enhancing the dissolution properties of relatively insoluble dietary supplements is provided in accordance with the invention. The method includes the steps of providing at least one relatively water insoluble dietary supplement, solubilizing the dietary supplement with a solubilizer, and incorporating an edible polyhydric alcohol into the solubilized dietary supplement to provide a liquid dietary supplement composition that can be dissolved in an aqueous system. The liquid dietary supplement composition can be readily supplied by incorporation in a gelatin capsule.

A gelatin capsule having a liquid dietary supplement incorporated therein is also provided in accordance with the invention. The gelatin capsule dissolves readily in the digestive tract and the dietary supplement has enhanced bioavailability in comparison to prior art gelatin capsules.

The invention accordingly comprises the several steps and the relation of one or more of such steps with respect to each of the others, and the composition possessing the features, properties, and the relation of constituents, which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
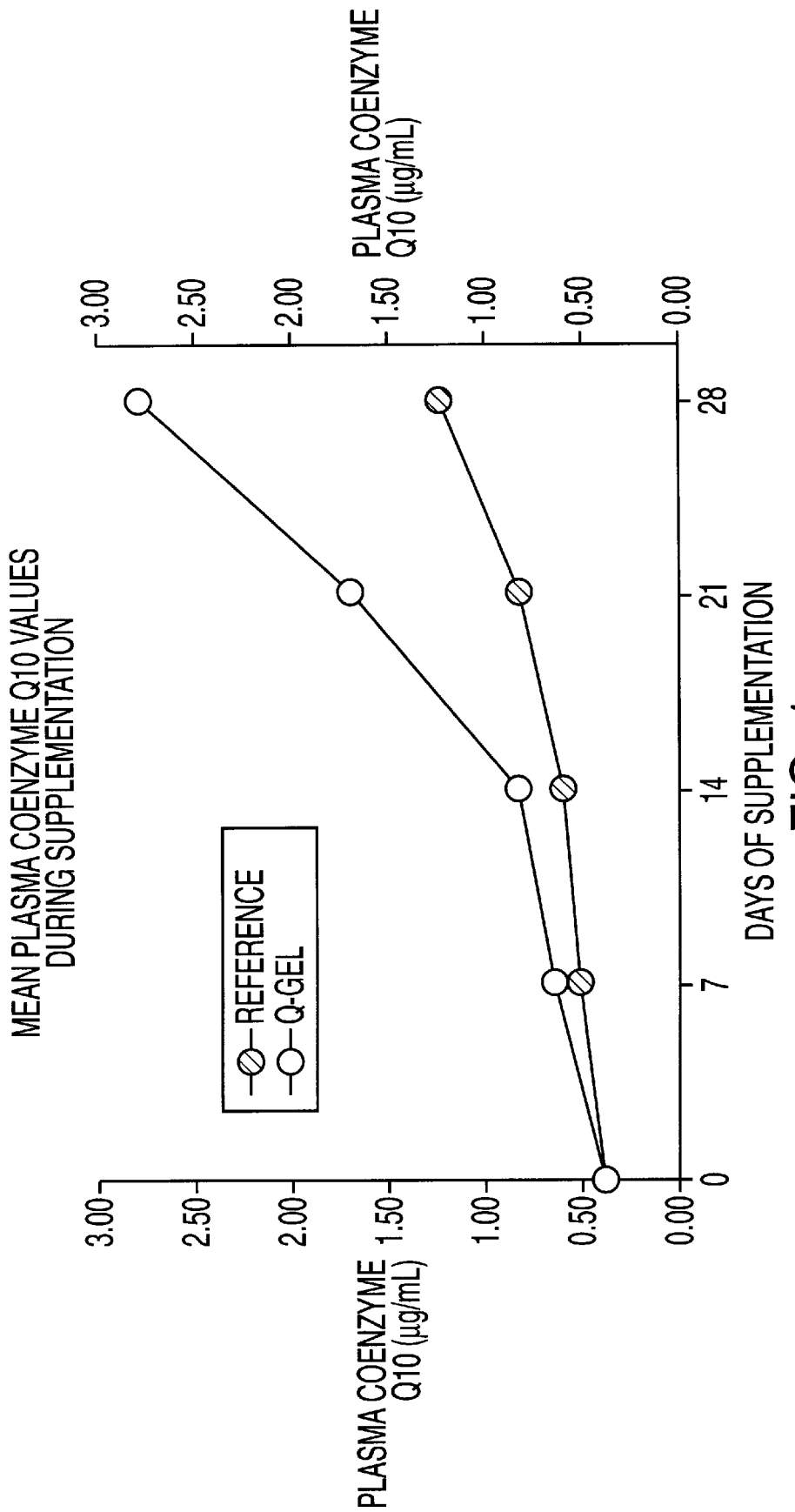
FIG. 1 is a graph showing Mean Plasma Coenzyme Q-10 Values During Supplementation for a reference control and a Coenzyme Q-10 product prepared in accordance with the invention.

The invention includes a method for enhancing the dissolution properties of relatively insoluble dietary supplements or therapeutic agents. The method includes the steps of providing at least one relatively water insoluble dietary supplement, solubilizing the dietary supplement with a solubilizer, and incorporating an edible polyhydric alcohol into the solubilized dietary supplement to provide a liquid dietary supplement composition that can be dissolved in an aqueous system. The liquid dietary supplement composition can be readily supplied by incorporation into a gelatin capsule or absorption onto a starch.

The dietary supplements or therapeutic agents that may be used in accordance with the invention is a virtually limitless list. In general, such therapeutic agents are relatively insoluble in water and the method provided enhances the dissolution properties of such agents so that they become soluble in the substantially aqueous system of the human digestive tract and solution will take place spontaneously with the minimum agitation which normally occurs due to peristaltic action in the gastrointestinal tract.

Suitable dietary supplements or therapeutic agents include, for example, micronutrients such as vitamins, minerals, and other nutritional co-factors. Exemplary agents include, but are not limited to, Coenzyme Q-10 (Ubiquinone), Tumeric Extract (Curcuminoids), Beta Carotene, Mixed Carotenoids Complex, Lutein, Lycopene, Tocotrieniols, Tocopherols (Vitamin E), Saw Palmetto Lipid Extract, Exhinacea Extract, Hawthorne Berry Extract, Ginseng Extract, Lipoic Acid (Thiotic Acid), Ascorbyl Palmitate, Kava Extract, St. John's Wort (Hypericum), Extract of Quercitin, Dihydrocpiandrosterone, Indol-3-carbinol, and mixtures thereof.

In particular, it is often advantageous to use combinations of therapeutic agents. For example, St. John's Wort and Kava Extract are believed to be useful for relief of depression and as a tranquilizing agent, respectively. Since the kavalactones, which are the active principals of the Kava Extract, and the hypericum, which is the active component of St. John's Wort, are all water insoluble, the method provided in accordance with the invention can be used to simultaneously solubilize all of the active components. Other combinations are also possible and desirable.

The dietary supplement or therapeutic agent is used in an amount between about 1 and 50% by weight of the solubilized composition, preferably in an amount between about 1 and 25% by weight, and more preferably in an amount between about 5 and 10%. When a mixture of therapeutic agents are used, the total amounts are within these ranges including combinations of both water soluble and water insoluble compounds with water insoluble compounds such as Ginko Biloba Extract and the Proanthocyanidines found in the extracts of Grape Seed and the bark of the French Maritime Pine.

The method provided in accordance with the invention requires that the dietary supplement or therapeutic agent be solubilized or dissolved in a solubilizer or surfactant. Such solubilizers are generally non-ionic surface active agents and must be generally recognized as safe (G.R.A.S.). The solubilizers may be complex esters or ester-ethers prepared from hexahydric alcohols, alkylene oxides, and fatty acids. Suitable solubilizers include Span type materials and Tween or Polysorbate type materials, which are known for use as emulsifiers, stabilizers, and thickeners in foods, cosmetics, and medicinal products.

In particular, Span type materials are partial esters of the common fatty acids, namely, lauric acid, palmitic acid, stearic acid, and oleic acids, and hexitol anhydrides, namely, hexitans and hexides, derived from sorbitol. In general, such sorbitan fatty acid esters have the structure:

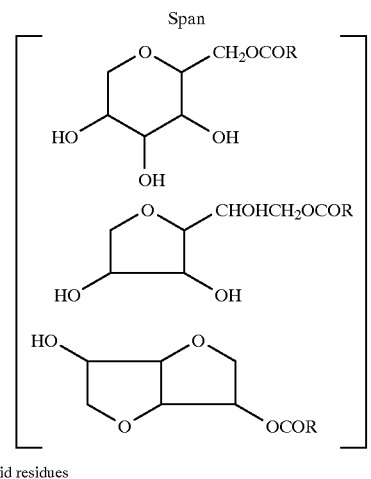

R = fatty acid residues when R is $OOC(C_{11}H_{23})$ the structure represents sorbitan laurate (Span 20); when R is $OOC(C_{17}H_{36})$ the structure represents sorbitan stearate (Span 60); and when R is $OOC(C_{17}H_{33})$ the structure represents sorbitan oleate (Span 80).

The hydrophilic character of the Span type materials is supplied by free hydroxyl and oxyethylene groups, while the lipophilic portion is found in the long chain fatty acids. These materials tend to be oil soluble and dispersible or insoluble in water. In a preferred embodiment of the present invention, at least a portion of the solubilizer is sorbitan monooleate.

The Tween or Polysorbate type materials are oleate esters of sorbitol and its anhydrides copolymerized with about 20 moles of ethylene oxide per mole of sorbitol and sorbitol anhydride. The Tween or Polysorbate type materials are derived from the Span type materials by adding polyoxyethylene chains to the nonesterified hydroxyls. The Tween type products are soluble or well dispersible in water. These oleate esters have the structure:

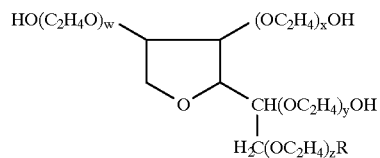

In a preferred embodiment, the Tween type material is a sorbitan mono-9-octadecenoate poly(oxy-1,2-ethanediyl) derivative wherein the sum of w, x, y, and z is 20 (Tween 80 or Polysorbate 80).

The solubilizer is used in an amount between about 20 and 90% by weight of the solubilized composition, preferably in an amount between about 35 and 80% by weight, more preferably in an amount between about 50 and 75%. In an especially preferred embodiment, the solubilizer is an mixture of a Span type material and a Tween type material. The ratio of Span type material: Tween type material can range between about 1 and 2 parts Span type material to between about 20 and 30 parts Tween type material, preferably about 1 part Span type material to about 9 parts Tween type material. Since Span type materials are generally oil soluble and dispersible or insoluble in water and Tween type materials are generally soluble or well dispersible in water, adjustment of ratio of the Span type materials to Tween type materials is effective for obtaining an appropriate degree of water solubility or insolubility of the solubilized composition, i.e. hydrophilic versus lipophilic properties.

The solubilized composition further includes an edible polyhydric alcohol. This component serves the important function of avoiding the necessity of slowly adding water to form an aqueous phase. In the absence of a polyhydric alcohol, a composition including a Span and/or Tween type emulsifier with a therapeutic agent therein would leave a firm gel upon dissolution of a gelatin capsule in which it could be contained. Such a firm gel would dissolve too slowly in the aqueous fluid of the digestive tract to be of any significant therapeutic benefit.

The edible polyhydric alcohol is preferably selected from the group consisting of propylene glycol, glycerol, and mixtures thereof. Edible propylene glycol has the structure 1,2-propanediol. Glycerol has the structure 1,2,3-propanetriol and is also known as glycerin.

The polyhydric alcohol is used in an amount between about 2 and 50% by weight of the solubilized composition, preferably between about 2 and 25% by weight, more preferably between about 4 and 20%.

The solubilized composition can readily be prepared by mixing the emulsifier and the polyhydric alcohol together. The mixture can be warmed to between about 50° and 60° C. and the therapeutic agent can be added.

The solubilized composition does not contain water and is, therefore, suitable for use in gelatin capsules, which can be prepared by conventional means. In particular, soft gelatin capsules generally contain liquid compositions, although even two-piece hard gelatin capsules may be used. The gelatin capsules are tasteless, easy to swallow and dissolve readily in the digestive tract. Once dissolved, the solubilized therapeutic agent spontaneously dissolves in the digestive fluids of the body with the minimal, slow agitation that occurs there. Alternatively, the solubilized composition may be absorbed onto a starch material and compressed to form tablets.

The following non-limiting Examples are presented for purposes of illustration only and are not to be construed in a limiting sense.

EXAMPLE 1

Six hundred and twenty-five grams (625 g) of Tween® 80, 125 g of Span® 80, and 150 g propylene glycol were mixed together and heated to between about 70° and 80° C. One hundred grams (100 g) of Curcumin (Tumeric Extract) was added with continued stirring until a clear solution resulted. The solubilized Curcumin composition was cooled to room temperature and filled into 1,000 soft gelatin capsules in an amount of 1,000 mg per capsule.

EXAMPLE 2

Four hundred and thirty-two grams (432 g) of Tween® 80, 85 g of Span® 80, and 100 g of glycerin were mixed together until a uniform solution resulted. The solution was warmed to between about 50° and 60° C. Fifty grams (50 g) of Kava extract containing 50% kavalactones was added and stirred until dissolution occurred. Three hundred and thirty-three grams (333 g) of St. John's Wort Extract containing 0.3% hypericum was added and stirred until a uniform suspension resulted. Although the hypericum, which is the active component of the St. John's Wort Extract dissolved in the solution, other inert components did not dissolve. The solubilized Kava extract and St. John's Wort Extract was filled into 1,000 soft gelatin capsules containing 25 mg of kavalactones and 1 mg of hypericum per capsule.

EXAMPLE 3

One hundred and fifty-five grams (155 g) of Tween® 60, 30 g of Span® 80, and 40 g of propylene glycol were mixed together and warmed to between about 40° and 50° C. Twenty-five grams (25 g) of Indole-3-carbinol was added and stirred until a clear solution resulted. The solubilized Indole-3-carbinole composition was used to fill 1,000 soft gelatin capsules at 250 mg of Indole-3-carbinole per capsule.

EXAMPLE 4

A Coenzyme Q-10 composition was prepared from 5.60% by weight of the solubilized composition of Span®80, 83.93% by weight of Tween® 80, 3.92%propylene glycol, and 3.55% Coenzyme Q-10. The solubilized Coenzyme Q-10 composition was incorporated into soft gelatin capsules. Testing of the capsules by the USP Dissolution method showed 100% dissolution of Coenzyme Q-10.

Each of the compositions prepared in accordance with Examples 1–4, inclusive, included a relatively water insoluble therapeutic agent in a solubilized form suitable for incorporation into a gelatin capsule. In preparing compositions of therapeutic agents, it is important to remember that the amount of active ingredients in any particular extract may have normal variations. Accordingly, it is often necessary to adjust the quantity of the extract used and the fill weight for each capsule in order to standardize the amount of active ingredient present in the capsule.

The solubilized compositions prepared in accordance with the invention result in greater bioavailability of the therapeutic agents when formulated in a gelatin capsule. Furthermore, since the therapeutic agent in each capsule is more bioavailable, the capsules can be prepared using smaller amounts of expensive therapeutic agents than prior art compositions. Plasma level studies have confirmed this observation.

Twenty-four (24) healthy volunteers were randomly assigned into two (2) groups. Each group contained three (3) white males, three (3) white females, three (3) black males, and three (3) black females. None of the volunteers had used Coenzyme Q-10 supplements prior to the study.

A first formulation of Reference Coenzyme Q-10 capsules was given to the first group of volunteers on a daily basis. The Reference Coenzyme Q-10 capsules contained Coenzyme Q-10 in a standard vegetable oil formulation.

A second formulation of Coenzyme Q-10 capsules prepared in accordance with Example 4 hereinabove (Q-Gel) was given to the second group of volunteers on a daily basis. The formulations of Coenzyme Q-10 were standardized to insure that each group of volunteers was receiving the same amount of Coenzyme Q-10.

The plasma Coenzyme Q-10 values of each volunteer were measured at 0, 7, 14, 21, and 28 days during supplementation. The Mean Plasma Coenzyme Q-10 Values for each group are graphically depicted in FIG. 1. As can be seen, the volunteers receiving the second formulation of Coenzyme Q-10 (Q-Gel) prepared in accordance with Example 4 had significantly higher plasma values indicating that the Coenzyme Q-10 was significantly more bioavailable.

Figure 2:
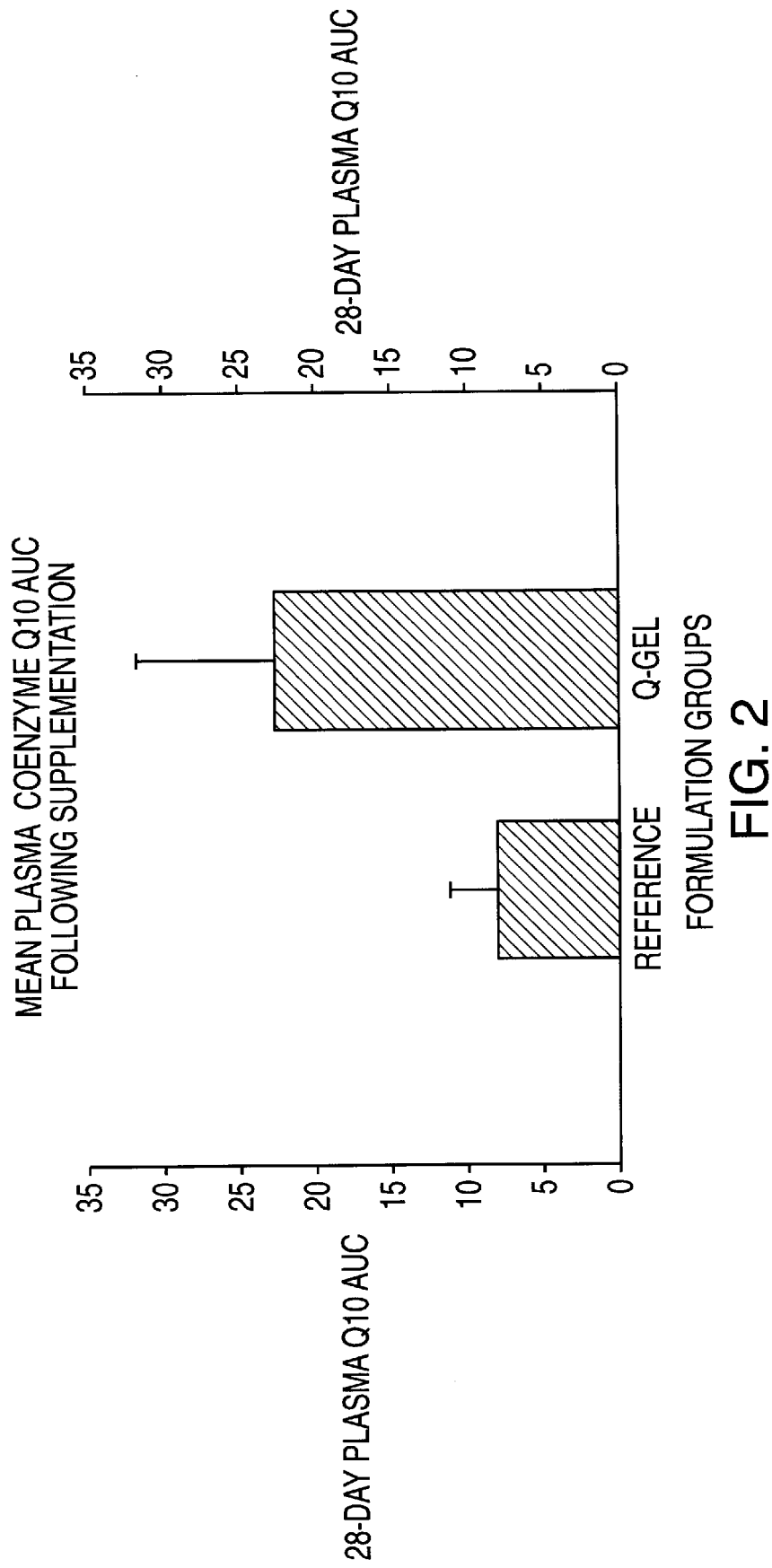
FIG. 2 is a graph showing Mean Plasma Coenzyme Q-10 AUC Following Supplementation for a reference and a Coenzyme Q-10 product prepared in accordance with the invention; and, FIG. 3 is a graph showing Percentage Comparison of 28-Day AUC for a reference and a Coenzyme Q-10 product prepared in accordance with the invention.
Figure 3:
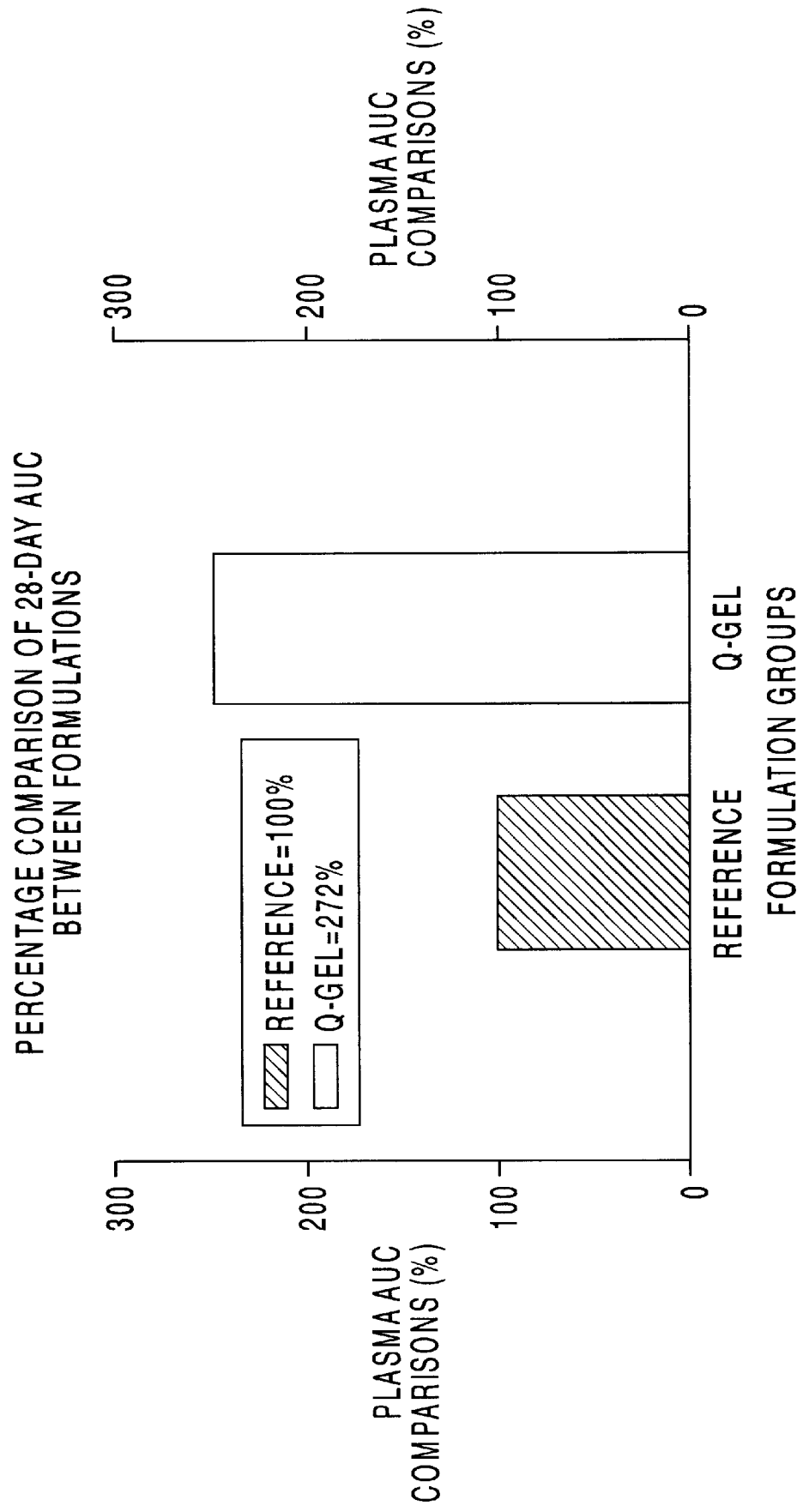

The Mean Plasma Coenzyme Q-10 Area Under Curve Following Supplementation for each group of volunteers is shown in FIG. 2 and The Percentage Comparison of 28-Day Area Under Curve Between Formulations is shown in FIG. 3. As can be seen, each of these means of assessment also reflected that the Coenzyme Q-10 obtained from the Q-Gel formulation was significantly more bioavailable than the Coenzyme Q-10 in the reference formulation.

It will thus be seen that the objects set forth above, among those made apparent from the preceding description, are efficiently obtained and, since certain changes may be made in carrying out the above method and in the composition set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A method for enhancing the dissolution and bioavailability properties of Coenzyme $Q_{10}$ (ubiquinone) from an orally delivered soft gelatin capsule in unit dosage form comprising filling a soft gelatin capsule with a uniform liquid non-aqueous solution containing an effective amount of Coenzyme $Q_{10}$, said non-aqueous solution being produced by the following steps:

mixing a non-ionic surface active agent as a solubilizer with a polyhydric alcohol to form a uniform mixture;

adding an effective amount of Coenzyme $Q_{10}$ for therapeutic use to said uniform mixture and mixing said Coenzyme $Q_{10}$ in said uniform mixture to form said uniform non-aqueous solution, said solubilizer being included in said non-aqueous solution in an amount ranging from about 20% to about 90% by weight and said polyhydric alcohol being included in said non-aqueous solution in an amount ranging from about 2% to about 50% by weight.

2. The method according to claim 1 wherein said solubilizer is a mixture of a sorbitan fatty acid ester and a copolymer of an oleate ester of sorbitol or sorbitol anhydride and (poly)ethylene oxide.

3. The method according to claim 2 wherein said sorbitan fatty acid ester and said copolymer are included in said solution in a weight ratio of about 1 to 2 parts fatty acid ester to about 20 to 30 parts copolymer.

4. The method according to claim 1 wherein said polyhydric alcohol is selected from the group consisting of propylene glycol, glycerol and mixtures thereof.

5. The method according to claim 3 wherein said polyhydric alcohol is selected from the group consisting of propylene glycol, glycerol and mixtures thereof.

6. The method according to claim 1 wherein said polyhydric alcohol is included in said solution in an amount ranging from about 2% to about 20% by weight.

7. The method according to claim 1 wherein said solubilizer is included in said solution in an amount ranging from about 35% to about 90% by weight.

8. The method according to claim 1 wherein said Coenzyme $Q_{10}$ is mixed in said uniform mixture at a temperature of about 50° C. to about 60° C.

9. A dietary supplement in unit dosage form as a soft gelatin capsule consisting essentially of a uniform non-aqueous composition formulated in a soft gelatin capsule, said non-aqueous composition consisting essentially of an effective amount of Coenzyme $Q_{10}$ (ubiquinone); and a uniform mixture of a non-ionic surface active agent as a solubilizer and a polyhydric alcohol into which said Coenzyme $Q_{10}$ is completely dissolved to form said non-aqueous composition, said solubilizer being included in said non-aqueous composition in an amount ranging from about 20% to about 90% by weight of said composition and said polyhydric alcohol being included in said composition in an amount ranging from about 2% to about 50% by weight of said composition.

10. The supplement according to claim 9 wherein said solubilizer is a mixture of a sorbitan fatty acid ester and a copolymer of an oleate ester of sorbitol or sorbitol anhydride and (poly)ethylene oxide.

11. The supplement according to claim 9 wherein said sorbitan fatty acid ester and said copolymer are included in said solution in a weight ratio of about 1 to 2 parts fatty acid ester to about 20 to 30 parts copolymer.

12. The supplement according to claim 9 wherein said polyhydric alcohol is selected from the group consisting of propylene glycol, glycerol and mixtures thereof.

13. The supplement according to claim 9 wherein said polyhydric alcohol is selected from the group consisting of propylene glycol, glycerol and mixtures thereof.

14. The supplement according to claim 9 wherein said polyhydric alcohol is included in said solution in an amount ranging from about 2% to about 20% by weight.

15. The supplement according to claim 9 wherein said solubilizer is included in said solution in an amount ranging from about 35 to about 90% by weight.

16. The supplement according to claim 1 wherein said Coenzyme $Q_{10}$ is mixed in said uniform mixture at a temperature of about 50° C. to about 60° C.

17. A non-aqueous Coenzyme $Q_{10}$ containing composition for oral administration in a soft gelatin capsule exhibiting favorable dissolution and bioavailability characteristics, said composition being prepared by the method of adding an effective amount of Coenzyme $Q_{10}$ (ubiquinone) to a solubilized composition consisting essentially of a uniform mixture of an amount of a solubilizer and an edible polyhydric alcohol effective in combination to solubilize said Coenzyme $Q_{10}$.

18. The composition according to claim 17 wherein said Coenzyme $Q_{10}$ is added to said solubilized composition at a temperature of about 50° C. to about 60° C.

19. The method according to claim 17 wherein said solubilizer is a mixture of a sorbitan fatty acid ester and a copolymer of an oleate ester of sorbitol or sorbitol anhydride and (poly)ethylene oxide.

20. The method according to claim 17 wherein said sorbitan fatty acid ester and said copolymer are included in said solution in a weight ratio of about 1 to 2 parts fatty acid ester to about 20 to 30 parts copolymer.

21. The method according to claim 17 wherein said polyhydric alcohol is selected from the group consisting of propylene glycol, glycerol and mixtures thereof.

22. The method according to claim 20 wherein said polyhydric alcohol is selected from the group consisting of propylene glycol, glycerol and mixtures thereof.

23. The method according to claim 17 wherein said polyhydric alcohol is included in said solution in an amount ranging from about 2% to about 20% by weight.

24. The method according to claim 17 wherein said solubilizer is included in said solution in an amount ranging from about 35% to about 90% by weight.

25. The method according to claim 17 wherein said Coenzyme $Q_{10}$ is mixed in said uniform mixture at a temperature of about 50° C. to about 60° C.

26. A dietary supplement in unit dosage form as a soft gelatin capsule consisting essentially of a uniform non-aqueous composition formulated in a soft gelatin capsule, said non-aqueous composition consisting essentially of:

an effective amount of Coenzyme $Q_{10}$ (ubiquinone) for therapeutic use; and a uniform mixture containing a solubilizer which includes a combination of a sorbitan fatty acid ester and a copolymer of an oleate ester of sorbitol or sorbitol anhydride and (poly)ethylene oxide and further including a polyhydric alcohol, said Coenzyme $Q_{10}$ being completely dissolved in said uniform mixture to form said non-aqueous composition, said sorbitan fatty acid ester and said copolymer of an oleate ester of sorbitol or sorbitol anhydride and (poly)ethylene oxide in combination being included in said non-aqueous composition in about 20% to about 90% by weight, said polyhydric alcohol being included in said composition in about 2% to about 20% by weight.

27. The supplement according to claim 26 wherein said fatty acid ester is sorbitan monooleate included in 5.60% by weight of said non-aqueous composition, said copolymer of an oleate ester of sorbitol or sorbitol anhydride and (poly)ethylene oxide is polyoxyethylene 20 sorbitan monooleate included in 83.93% by weight of said non-aqueous composition, said propylene glycol is included in 3.92% by weight of said non-aqueous composition and said Coenzyme $Q_{10}$ is included in 3.55% by weight of said non-aqueous composition.

28. The composition according to claim 26 wherein said Coenzyme $Q_{10}$ is dissolved in said mixture at a temperature ranging from about 50° C. to about 60° C.

29. A method for enhancing the dissolution properties of Coenzyme $Q_{10}$ comprising:

providing at least one non-aqueous solubilizer selected from the group consisting of sorbitan fatty acid esters; copolymers of sorbitol or sorbitol anhydride with (poly)ethylene oxide; and mixtures thereof;

providing at least one edible polyhydric alcohol selected from the group consisting of propylene glycol, glycerol, and mixtures thereof;

mixing the at least one non-aqueous solubilizer and the at least one polyhydric alcohol to form a uniform solution;

adding Coenzyme $Q_{10}$ to the uniform solution to provide a solubilized dietary supplement composition having enhanced dissolution properties; and, incorporating the solubilized dietary supplement composition into at least one soft gelatin capsule for ingestion.

30. The method of claim 29 wherein the at least one non-aqueous solubilizer is used in an amount between about 20% and about 90% by weight of the solubilized composition.

31. The method of claim 29 wherein the edible polyhydric alcohol is used in an amount between about 2% and about 50% by weight of the solubilized composition.

32. The method of claim 29 further comprising the step of warming the uniform solution to a temperature between about 40° and about 80° C. prior to adding the at least one dietary supplement.

33. The method of claim 29 wherein the Coenzyme $Q_{10}$ is present in an amount between about 1% and 50% by weight of the solubilized composition.

34. The method of claim 32 further comprising the step of cooling the solubilized dietary supplement composition having enhanced dissolution properties to room temperature prior to incorporating the solubilized dietary supplement composition into the at least one soft gelatin capsule.

35. A solubilized Coenzyme $Q_{10}$ composition having enhanced dissolution properties comprising:

between about 1% and 50% by weight of Coenzyme $Q_{10}$;

between about 20% and about 90% by weight of at least one non-aqueous solubilizer selected from the group consisting of sorbitan fatty acid esters; copolymers of sorbitol or sorbitol anhydride with (poly)ethylene oxide; and mixtures thereof; and, between about 2% and about 50% by weight of at least one edible polyhydric alcohol selected from the group consisting of glycol, glycerol, and mixtures thereof.

36. The solubilized Coenzyme $Q_{10}$ composition of claim 34 incorporated into a soft gelatin capsule.

* * * * *